United States Patent [19]

Pales

[11] Patent Number: 5,010,901
[45] Date of Patent: Apr. 30, 1991

[54] DEVICE FOR PREVENTING SUCKING OF THUMB OR FINGER

[76] Inventor: Jaime M. Pales, Calle Mendez Vigo 343, Dorado, P.R. 00646

[21] Appl. No.: 778,484

[22] Filed: Sep. 20, 1985

[51] Int. Cl.⁵ .............................................. A61F 13/10
[52] U.S. Cl. ................................................ 128/880
[58] Field of Search ............................ 446/327–329; 128/880

[56] References Cited

U.S. PATENT DOCUMENTS

| | | | |
|---|---|---|---|
| 1,048,569 | 12/1912 | Mitchell | 128/133 |
| 1,652,867 | 12/1927 | MacLachlan | 128/133 |
| 1,990,384 | 2/1935 | Klohs | 128/133 |
| 2,074,762 | 3/1937 | Seyfried | 128/157 |
| 2,225,896 | 12/1940 | Belknap | 128/133 |
| 2,498,122 | 2/1950 | Haniuk | 128/133 X |
| 2,586,608 | 2/1952 | Bryson | 128/359 X |
| 2,688,961 | 9/1954 | Thomas | 128/359 X |
| 2,798,482 | 7/1957 | Feeney | 128/359 X |
| 2,852,885 | 9/1958 | Mayer | 446/327 |
| 3,056,154 | 10/1962 | Neal | 15/104 |
| 3,442,267 | 5/1969 | Krygier | 128/359 X |
| 4,396,014 | 8/1983 | Pace et al. | 128/133 |
| 4,545,378 | 10/1985 | Chromes | 128/359 |

*Primary Examiner*—Richard J. Apley
*Assistant Examiner*—Rachel M. Healey
*Attorney, Agent, or Firm*—Scrivener and Clarke

[57] ABSTRACT

A glove to be worn by one who habitually sucks one or more the the digits (thumb or finger) of the hand has a tubular part which encloses the sucked digits(s) and which has on its external surface adjacent its outer end the representation of a human figure having a face and a hat the brim of which is formed by a flange which extends outwardly from the tubular part.

2 Claims, 1 Drawing Sheet

DEVICE FOR PREVENTING SUCKING OF THUMB OR FINGER

A glove is provided which has a tubular part which encloses the digit (the thumb or a finger) which a child habitually sucks, which part has adjacent its outer end the representation of a human face or figure wearing a hat, and an annular flange surrounds and protrudes from the digit enclosing part at the position of the brim of the hat to prevent further insertion of the enclosed digit into the mouth.

DESCRIPTION OF THE PREFERRED EMBODIMENT OF THE INVENTION

Figure 1:
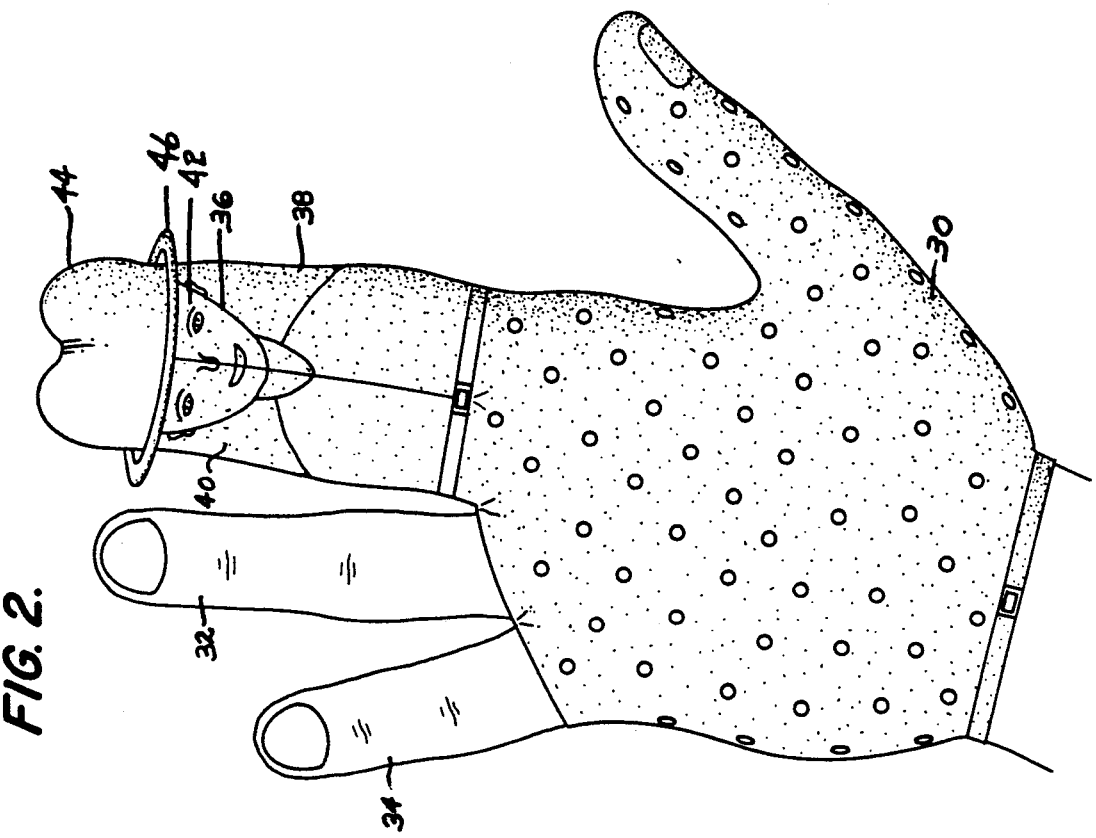
FIG. 1 is a plan view of the human hand having on it the glove provided by the invention, with means for preventing sucking of a digit, which is the thumb.

The preferred embodiment of the invention is disclosed in FIG. 1 in association with the human hand, the left hand being illustrated although the invention is equally useful with either hand. The invention takes the form of a partial glove for the hand, and in its preferred embodiment comprises a tubular closed-end digit receiving part 2 which receives and encases the thumb, a wrist-encircling part 4, and a part 6 which connects these two parts and surrounds the base of the thumb and has an upper edge 8 which extends diagonally across the lower areas of the palm and the back of the hand 10. The wrist encircling part 4 is so constructed that a child wearing the partial glove cannot remove it and, to accomplish this, the wrist encircling part 4 is formed as a unitary band which tightly encircles the wrist at its juncture with the hand.

In further accordance with the preferred form of the invention the tubular closed end digit receiving part 2 has on its external surface and adjacent its closed end the representation 20 of a human figure having a head 22 and wearing a hat 24. At the location of the brim of the hat the digit receiving part 2 is provided with an external annular flange 26 which has the dual function of completing the hat worn by the human figure representation, and also providing adjacent the outer end of the thumb an annular outwardly extending flange or wall which prevents insertion of the thumb into the mouth.

Figure 2:
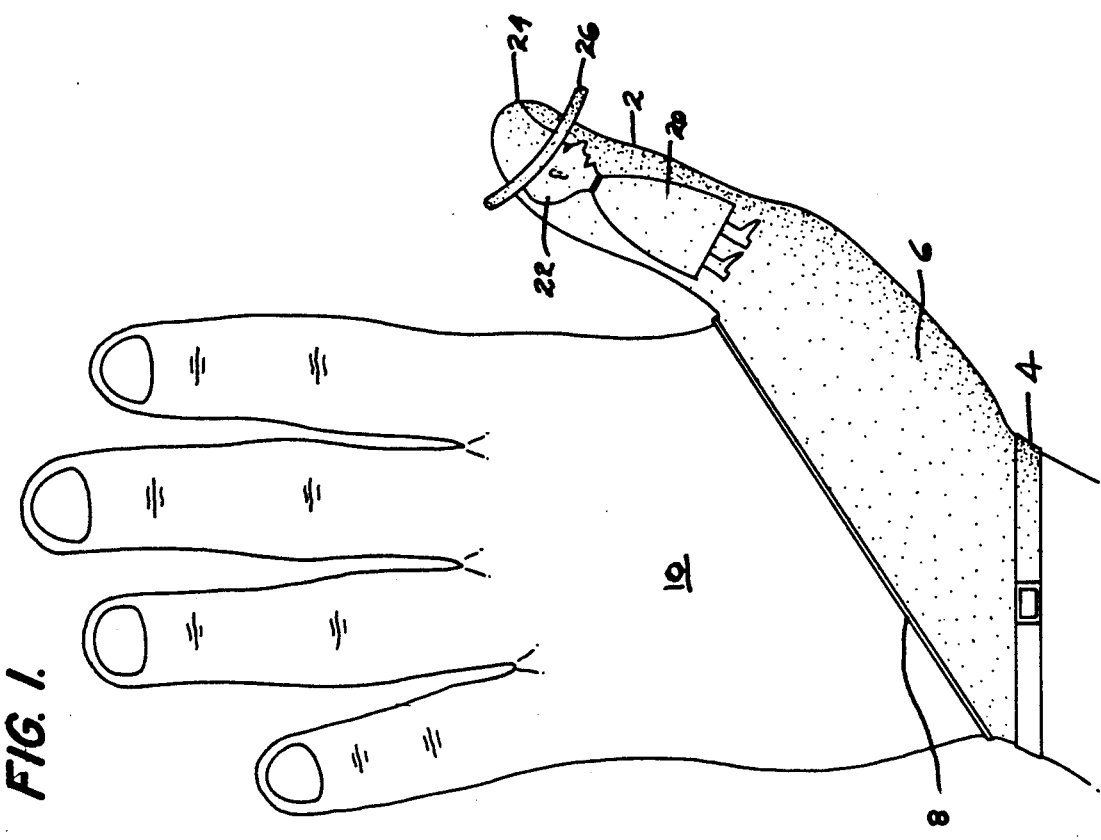
FIG. 2 is a view similar to FIG. 1 with means for preventing sucking of the index and middle digits.

A second form which the invention may take is disclosed in FIG. 2, and in this embodiment the glove 30 encloses the entire hand of the wearer except only the ring and little fingers 32, 34 respectively, and is provided with a tubular digit receiving part 36 which encloses the index and middle fingers 38, 40 as a unit. This finger enclosing part 36 has on its external surface and adjacent its closed end the representation of a human figure having a face 42 and wearing a hat 44, the brim of which is formed by a flange 46 which surrounds and extends outwardly from the tubular part 36 to prevent insertion of the two enclosed fingers into the mouth.

I claim:

1. A device for preventing sucking of at least one of the digits of the human hand, comprising:
   (a) a glove having a part encircling the wrist and at least a part of the hand, and a tubular part shaped to closely enclose at least one of the digits and having a closed outer end,
   (b) an annular flat flange extending radially outwardly from the tubular part a distance such as to prevent insertion thereof into the mouth and at a position spaced downwardly from said closed outer end to which when said glove is in its position of use is adjacent to but below the outer end of said at least one digit.

2. The device of claim 1 wherein the exterior of the tubular part has on its exterior surface adjacent the closed outer end the representation of a human face wearing a hat, said annular flat flange representing the brim of said hat.

* * * * *